(12) United States Patent
Campbell et al.

(10) Patent No.: US 7,321,075 B2
(45) Date of Patent: Jan. 22, 2008

(54) SERIAL NUCLEAR TRANSFER OF UNGULATE EMBRYOS

(75) Inventors: Keith Henry Stockman Campbell, Midlothian (GB); Ian Wilmut, Midlothian (GB)

(73) Assignee: Roslin Institute (Edinburgh), Midlothian (GB)

( * ) Notice: Subject to any disclaimer, the term of this patent is extended or adjusted under 35 U.S.C. 154(b) by 717 days.

(21) Appl. No.: 10/234,854

(22) Filed: Sep. 5, 2002

(65) Prior Publication Data

US 2003/0106081 A1  Jun. 5, 2003

Related U.S. Application Data

(63) Continuation of application No. 10/118,337, filed on Apr. 9, 2002, now abandoned, which is a continuation of application No. 09/989,125, filed on Nov. 21, 2001, which is a continuation of application No. 09/650,285, filed on Aug. 29, 2000, now Pat. No. 6,525,243, application No. 10/234,854, which is a continuation of application No. 10/151,304, filed on May 21, 2002, now abandoned, which is a continuation of application No. 09/989,128, filed on Nov. 21, 2001, which is a continuation of application No. 09/650,285, application No. 10/234,854, which is a continuation of application No. 10/151,305, filed on May 21, 2002, now abandoned, which is a continuation of application No. 09/989,126, filed on Nov. 21, 2001, which is a continuation of application No. 09/650,285, which is a continuation of application No. 08/803,165, filed on Feb. 19, 1997, now Pat. No. 6,252,133, which is a continuation of application No. PCT/GB96/02098, filed on Aug. 30, 1996.

(30) Foreign Application Priority Data

Aug. 31, 1995  (GB) ................................. 9517779.6

(51) Int. Cl.
*C12N 15/00* (2006.01)
*C12N 5/00* (2006.01)

(52) U.S. Cl. .................. 800/24; 435/375; 435/377
(58) Field of Classification Search .................. 800/24, 800/14–17; 435/375, 377, 373
See application file for complete search history.

(56) References Cited

U.S. PATENT DOCUMENTS

| | | | |
|---|---|---|---|
| 5,480,772 A | 1/1996 | Wangh | |
| 5,496,720 A | 3/1996 | Susko-Parrish et al. | |
| 5,523,226 A | 6/1996 | Wheeler | |
| 6,147,276 A | 11/2000 | Campbell et al. | |
| 6,252,133 B1 | 6/2001 | Campbell et al. | |
| 6,525,243 B1 | 2/2003 | Campbell et al. | |

FOREIGN PATENT DOCUMENTS

| | | |
|---|---|---|
| CA | 2092258 | 3/1993 |
| CA | 2059199 | 7/1993 |
| GB | 2265909 | 10/1993 |
| WO | WO94/06422 | 3/1994 |
| WO | WO94/18344 | 8/1994 |
| WO | WO95/03795 | 2/1995 |
| WO | WO96/07732 | 9/1995 |
| WO | WO99/36510 | 7/1999 |

OTHER PUBLICATIONS

Mitalipov et al. Rhesus Monkey Embryos Produced by Nuclear Transfer from Embryonic Blastomeres or Somatic Cells. Biol. Reproduct. 2002, vol. 66, pp. 1367-1373.*
Pennisi and Vogel. Cloning: A Hard Act to Follow. Science. Jun. 9, 2000, vol. 288, pp. 1722-1727.*
Fitchev et al. Nuclear Transfer in the Rat: Potential Access to the Germline. Transplantation Proceed. 1999, vol. 31, pp. 1525-1530.*
Chense et al. Cloned Rabbits Produced by Nuclear Transfer from Adult Somatic Cells. Nature Biotechnology. Apr. 2002, vol. 20, pp. 366-369.*
Galli et al. A Cloned Horse Born to Its Dam Twin. Nature. Aug. 7, 2003, vol. 424, pp. 635.*
Wakayama et al. Full-Term Development of Mice from Enucleated oocytes Injected with Cumulus Cell Nuclei. Nature. Jul. 23, 1998, vol. 394, pp. 369-374.*
Zhou et al. Generation of Fertile Cloned Rats by Regulating Oocyte Activation. Science. Nov. 14, 2003, vol. 302, pp. 1179.*
Bradley, *Biotechnology* 10:534-539 (1992).
Briggs & King, *Proc. Natl. Acad. Sci* USA 38 455-461 (1952).
Bromhall, J.D., Nuclear transplantation in the rabbit egg, *Nature*, vol. 258, No. 5537, pp. 719-722, Dec. 25, 1975.
Campbell, *Biol. Reprod.* 50 1385-1393 (1994).
Campbell, *Therio.* 43 181 (1995).
Campbell, *J. Reprod. Fertil.* Abstract Series 5 31 (1995) Abstract No. 86.

(Continued)

*Primary Examiner*—Deborah Crouch
(74) *Attorney, Agent, or Firm*—Finnegan, Henderson, Farabow, Garrett & Dunner, LLP

(57) ABSTRACT

A method of reconstituting an animal embryo involves transferring a diploid nucleus into an oocyte which is arrested in the metaphase of the second meiotic division. The oocyte is not activated at the time of transfer, so that the donor nucleus is kept exposed to the recipient cytoplasm for a period of time. The diploid nucleus can be donated by a cell in either the G0 or G1 phase of the cell cycle at the time of transfer. Subsequently, the reconstituted embryo is activated. Correct ploidy is maintained during activation, for example, by incubating the reconstituted embryo in the presence of a microtubule inhibitor such as nocodazole. The reconstituted embryo may then give rise to one or more live animal births. The invention is useful in the production of transgenic animals as well as non-transgenics of high genetic merit.

8 Claims, 1 Drawing Sheet

OTHER PUBLICATIONS

Campbell, K.H.S. et al., "Live Lambs by Nuclear Transfer Frm an Established Cell Line", *Theriogenology* 45(1) 1996, 287, ISSN: 0083-691X.

Campbell, K.H.S. et al., "Nuclear-cytoplasmic interactions during the first cycle of nuclear transfer reconstructed bovine embryos: implications from desoxyribonucleic acid replication and development" *Biology of Reproduction*, vol. 49, No. 1, Nov. 1993, pp. 933-942.

Campbell, K.H.S. et al., "Sheep Cloned by Nuclear Transfer From A Cultured Cell Line", *Nature*, vol. 380, Mar. 7, 1996, p. 64.

Campbell & Wilmut, *Vth World Congress on Genetics as Applied to Livestock* 20 180-187 (1994).

Collas, P. et al., "Factors affecting the efficiency of nuclear transplantation in the rabbit embryo", *Biology of Reproduction*, vol. 43, No. 5, Nov. 1990, pp. 877-884.

Collas et al., *Biol. Reprod.*, 46 501-511 (1992).

Collas et al. *Mol. Reprod. & Devel.*, 38 264-267 (1994).

Collas & Robl, *Biol. Reprod.*, 45 455-465 (1991).

Cutbertson & Cobbold, *Nature* 316 541-542 (1985).

Czolowska, R. et al., "Behavior of thymocyte nuclei in non-activated and activated mouse oocytes", *Journal of Cell Science*, vol. 69, 1984, see p. 27, line 1-p. 33, line 3; table 1.

Delhaise et al., *Reprod.* Fertility, 7 1217-1219 (1995).

Esikov, *Development* 109 322-328 (1990) [Copyright Protected—Not provided herein].

Finch, *Biochem Soc. Trans.* 24 369S (1996).

Freeman & Beitz, In Symposium on Cloning Mammals by Nuclear Transplantation (Seidel, GE Jr. ed.) 17-20 *Colorado State University, Colorado* (1992).

Fulka et al. (1998) BioEssays 20, 847-851.

Gardner, *Biology of Reproduction* 50 390-400 (1994).

Greaham, C.F., "The fusion of cells with one-and two-cell mouse embryo", *The Wistar Institute Symposium Monograph*, vol. 9, Jan. 1, 1969.

Gurdon, QJ Microsc. Soc. 101 299-311 (1960).

Hope, P.C., & Illmensee, K., *Proc. Nat'l Acad. Sci. USA* 74 5657-5661 (1977).

Hoppe, P.C., & Illmensee, K. *Proc. Nat'l Acad. Sci. USA* 79 1912-1916 (1982).

Howlett & Bolton, *J. Embryol. Exp. Morpho.* 87 175-206 [Copyright Protected—Not provided herein].

Illmensee, K., & Hoppe, P.C., *Cell* 23 9-18 (1981).

Kanka, *Mol. Reprod. Dav.* 29 110-116 (1991).

Keefer et al., *Biol. Reprod.*, 50 935-939 (1994).

Kono et al., *Theriogenology*, 35 227 (1991).

Lavoir et al., *Biol. Reprod.*, 56 194-199 (1997).

Leno & Munshi, *J. Cell Biol. 127* (1) 5-14 (1994).

Modlinski et al. *Development* 108 337-348 (1990).

Otaegui, P.J. et al., "Transfer of nuclei from 8-cell stage mouse embryos following use of nocodazole to control the cell cycle" *Molecular Reproduction and Development*, vol. 39, No. 2, Oct. 1, 1994, pp. 147-152.

Ozil, *Development* 109 117-127 (1990) [Copyright Protected-Not provided].

Prather & First, *J. Reprod. Fertil. Suppl.* 41 125 (1980).

Prather, *Biol Reprod.* 37 859-866 (1987).

Prather et al. *Biology of Reproduction* 41 414-418 (1989).

Prather, *J. Exp. Zool.* 225 355-358 (1990).

Richie & Campbell, *J. Reprod. Fertil. Abstract Series 15 60* (1995) Abstract No. 175.

Robertson, E.J., *Teratocarcinomas & embryonic stem cells: a practical approachl*, 71-112, IRL Press Oxford (1987).

Robl, Symposium on Cloning Mammals by Nuclear Transplantation (Seidel ed.) *Colorado State University* 24-27 (1992).

Saito et al., *Develop. Biol.* 201 134-141 (1992).

Seamark, *Reprod. Fertil. & Devel.* 6 (5) 653 (1994) Abstract No. 95:4100.

Sims et al. (1993) *Proced. Natl. Acad. Sci.* 90, 6143-6147.

Smith & Wilmut, *Biol. Reprod.* 40 1027-1035 (1989).

Solter, *Nature*, 380 24-25 (1996).

Spemann, *Embryonic Development & Induction*, 210-211 Hofner Publishing Co., New York (1938).

Stanton, *Brain Physiology* 2 71-83 (1992).

Stice et al., *Biol. Reprod.*, 54 100-110 (1996).

Szollosi et al., *J. Cell Science*, 91 (Pt. 4) 603-613 (1988).

Thompson, *Biology of Reproduction* 53 1385-1391 (1995).

Tsunoda, *J. Reprod. Fertil.* 82 173 (1988).

Tsunoda, *J. Reprod. & Fertil* 98 537-540 (1993).

Westhusin, *Biol. Reprod.* (*Suppl.*) 42 176 (1990) Abstract No. 407.

Wheeler, *Reprod. Fertil. Dev.* 6 563-568 (1994).

Whitfield, *Control of Animal Cell Proliferation* 1 331-365 (1985).

Whittingham & Wales, *Aust. J. Biol. Sci.* 22 1065-1068 (1969).

Willadesen, *In Mammalian Egg Transfer* (Adams, E.E., ed.) 185 CRC Press, Boca Raton, Florida (1982).

Willadsen, S.M. "Nuclear transplantation in sheep embroys", *Nature*, vol. 320, No. 6, Mar. 1986, London, GB.

Wilmut et al. (1997) *Nature* 385, 810-813.

* cited by examiner

SERIAL NUCLEAR TRANSFER OF UNGULATE EMBRYOS

This is a continuation of application Ser. No. 10/118,337 filed Apr. 9, 2002, now abandoned which is a continuation of Ser. No. 09/989,125 filed Nov. 21, 2001, which is a continuation of Ser. No. 09/650,285 filed Aug. 29, 2000, now U.S. Pat. No. 6,525,243. This is also a continuation of application Ser. No. 10/151,304 filed May 21, 2002, now abandoned which is a continuation of Ser. No. 09/989,128 filed Nov. 21, 2001, which is a continuation of Ser. No. 09/650,285 filed Aug. 29, 2000, now U.S. Pat. No. 6,525,243. This is also a continuation of application Ser. No. 10/151,305 filed May 21, 2002, now abandoned which is a continuation of Ser. No. 09/989,126 filed Nov. 21, 2001, which is a continuation of Ser. No. 09/650,285 filed Aug. 29, 2000, now U.S. Pat. No. 6,525,243. Ser. No. 09/650,285 is a continuation of application Ser. No. 08/803,165, filed Feb. 19, 1997 (now U.S. Pat. No. 6,252,133), which is a continuation of PCT/GB96/02098, filed on Aug. 30, 1996, which claims the benefit of British application GB 9517779.6, filed on Aug. 31, 1995, all of which are incorporated herein by reference.

This invention relates to the generation of animals including but not being limited to genetically selected and/or modified animals, and to cells useful in their generation.

The reconstruction of mammalian embryos by the transfer of a donor nucleus to an enucleated oocyte or one cell zygote allows the production of genetically identical individuals. This has clear advantages for both research (i.e. as biological controls) and also in commercial applications (i.e. multiplication of genetically valuable livestock, uniformity of meat products, animal management).

Embryo reconstruction by nuclear transfer was first proposed (Spemann, *Embryonic Development and Induction* 210–211 Hofner Publishing Co., New York (1938)) in order to answer the question of nuclear equivalence or 'do nuclei change during development?'. By transferring nuclei from increasingly advanced embryonic stages these experiments were designed to determine at which point nuclei became restricted in their developmental potential. Due to technical limitations and the unfortunate death of Spemann these studies were not completed until 1952, when it was demonstrated in the frog that certain nuclei could direct development to a sexually mature adult (Briggs and King, *Proc. Natl. Acad. Sci. USA* 38 455–461 (1952)). Their findings led to the current concept that equivalent totipotent nuclei from a single individual could, when transferred to an enucleated egg, give rise to "genetically identical" individuals. In the true sense of the meaning these individuals would not be clones as unknown cytoplasmic contributions in each may vary and also the absence of any chromosomal rearrangements would have to be demonstrated.

Since the demonstration of embryo cloning in amphibians, similar techniques have been applied to mammalian species. These techniques fall into two categories:
1) transfer of a donor nucleus to a matured metaphase II oocyte which has had its chromosomal DNA removed and
2) transfer of a donor nucleus to a fertilised one cell zygote which has had both pronuclei removed. In ungulates the former procedure has become the method of choice as no development has been reported using the latter other than when pronuclei are exchanged.

Transfer of the donor nucleus into the oocyte cytoplasm is generally achieved by inducing cell fusion. In ungulates fusion is induced by application of a DC electrical pulse across the contact/fusion plane of the couplet. The same pulse which induces cell fusion also activates the recipient oocyte. Following embryo reconstruction further development is dependent on a large number of factors including the ability of the nucleus to direct development i.e. totipotency, developmental competence of the recipient cytoplast (i.e. oocyte maturation), oocyte activation, embryo culture (reviewed Campbell and Wilmut in *Vth World Congress on Genetics as Applied to Livestock* 20 18–187 (1994)).

In addition to the above we have shown that maintenance of correct ploidy during the first cell cycle of the reconstructed embryo is of major importance (Campbell et al., *Biol. Reprod.* 49 933–942 (1993); Campbell et al., *Biol. Reprod.* 50 1385–1393 (1994)). During a single cell cycle all genomic DNA must be replicated once and only once prior to mitosis. If any of the DNA either fails to replicate or is replicated more than once then the ploidy of that nucleus at the time of mitosis will be incorrect. The mechanisms by which replication is restricted to a single round during each cell cycle are unclear, however, several lines of evidence have implicated that maintenance of an intact nuclear membrane is crucial to this control. The morphological events which occur in the donor nucleus after transfer into an enucleated metaphase II oocyte have been studied in a number of species including mouse (Czolowiska et al., *J. Cell Sci.* 69 19–34 (1984)), rabbit (Collas and Robl, *Biol. Reprod.* 45 455–465 (1991)), pig (Prather et al., *J. Exp. Zool.* 225 355–358 (1990)), cow (Kanka et al., *Mol. Reprod. Dev.* 29 110–116 (1991)). Immediately upon fusion the donor nuclear envelope breaks down (NEBD), and the chromosomes prematurely condense (PCC). These effects are catalysed by a cytoplasmic activity termed maturation/mitosis/meiosis promoting factor (MPF). This activity is found in all mitotic and meiotic cells reaching a maximal activity at metaphase. Matured mammalian oocytes are arrested at metaphase of the 2nd meiotic division (metaphase II) and have high MPF activity. Upon fertilisation or activation MPF activity declines, the second meiotic division is completed and the second polar body extruded, the chromatin then decondenses and pronuclear formation occurs. In nuclear transfer embryos reconstructed when MPF levels are high NEBD and PCC occur; these events are followed, when MPF activity declines, by chromatin decondensation and nuclear reformation and subsequent DNA replication. In reconstructed embryos correct ploidy can be maintained in one of two ways; firstly by transferring nuclei at a defined cell cycle stage, e.g. diploid nuclei of cells in G1, into metaphase II oocytes at the time of activation; or secondly by activating the recipient oocyte and transferring the donor nucleus after the disappearance of MPF activity. In sheep this latter approach has yielded an increase in the frequency of development to the blastocyst stage from 21% to 55% of reconstructed embryos when using blastomeres from 16 cell embryos as nuclear donors (Campbell et al., *Biol. Reprod.* 50 1385–1393 (1994)).

These improvements in the frequency of development of reconstructed embryos have as yet not addressed the question of nuclear reprogramming. During development certain genes become "imprinted" i.e. are altered such that they are no longer transcribed. Studies on imprinting have shown that this "imprinting" is removed during germ cell formation (i.e. reprogramming). One possibility is that this reprogramming is affected by exposure of the chromatin to cytoplasmic factors which are present in cells undergoing meiosis. This raises the question of how we may mimic this situation during the reconstruction of embryos by nuclear transfer in order to reprogram the developmental clock of the donor nucleus.

It has now been found that nuclear transfer into an oocyte arrested in metaphase II can give rise to a viable embryo if normal ploidy (i.e. diploidy) is maintained and if the embryo is not activated at the time of nuclear transfer. The delay in activation allows the nucleus to remain exposed to the recipient cytoplasm.

According to a first aspect of the present invention there is provided a method of reconstituting an animal embryo, the method comprising transferring a diploid nucleus into an oocyte which is arrested in the metaphase of the second meiotic division without concomitantly activating the oocyte, keeping the nucleus exposed to the cytoplasm of the recipient for a period of time sufficient for the reconstituted embryo to become capable of giving rise to a live birth and subsequently activating the reconstituted embryo while maintaining correct ploidy. At this stage, the reconstituted embryo is a single cell.

In principle, the invention is applicable to all animals, including birds such as domestic fowl, amphibian species and fish species. In practice, however, it will be to non-human animals, especially non-human mammals, particularly placental mammals, that the greatest commercially useful applicability is presently envisaged. It is with ungulates, particularly economically important ungulates such as cattle, sheen, goats, water buffalo, camels and pigs that the invention is likely to be most useful, both as a means for cloning animals and as a means for generating transgenic animals. It should also be noted that the invention is also likely to be applicable to other economically important animal species such as, for example, horses, llamas or rodents, e.g. rats or mice, or rabbits.

The invention is equally applicable in the production of transgenic, as well as non-transgenic animals. Transgenic animals may be produced from genetically altered donor cells. The overall procedure has a number of advantages over conventional procedures for the production of transgenic (i.e. genetically modified) animals which may be summarised as follows:

(1) fewer recipients will be required;
(2) multiple syngeneic founders may be generated using clonal donor cells;
(3) subtle genetic alteration by gene targeting is permitted;
(4) all animals produced from embryos prepared by the invention should transmit the relevant genetic modification through the germ line as each animal is derived from a single nucleus; in contrast, production of transgenic animals by pronuclear injection or chimerism after inclusion of modified stem cell populations by blastocyst injection produces a proportion of mosaic animals in which all cells do not contain the modification and may not transmit the modification through the germ line; and
(5) cells can be selected for the site of genetic modification (e.g. integration) prior to the generation of the whole animal.

It should be noted that the term "transgenic", in relation to animals, should not be taken to be limited to referring to animals containing in their germ line one or more genes from another species, although many transgenic animals will contain such a gene or genes. Rather, the term refers more broadly to any animal whose germ line has been the subject of technical intervention by recombinant DNA technology. So, for example, an animal in whose germ line an endogenous gene has been deleted, duplicated, activated or modified is a transgenic animal for the purposes of this invention as much as an animal to whose germ line an exogenous DNA sequence has been added.

In embodiments of she invention in which the animal is transgenic, the donor nucleus is genetically modified. The donor nucleus may contain one or more transgenes and the genetic modification may take place prior to nuclear transfer and embryo reconstitution. Although micro-injection, analogous to injection into the male or female pronucleus of a zygote, may be used as a method of genetic modification, the invention is not limited to that methodology: mass transformation or transfection techniques can also be used e.g. electroporation, viral transfection or lipofection.

In the method of the invention described above, a diploid nucleus is transferred from a donor into the enucleated recipient oocyte. Donors which are diploid at the time of transfer are necessary in order to maintain the correct ploidy of the reconstituted embryo; therefore donors may be either in the G1 phase or preferably, as is the subject of our co-pending PCT patent application No. PCT/GB96/02099 filed today (claiming priority from GB 9517780.4), in the G0 phase of the cell cycle.

The mitotic cell cycle has four distinct phases, G, S, G2 and M. The beginning event in the cell cycle, called start, takes place in the G1 phase and has a unique function. The decision or commitment to undergo another cell cycle is made at start. Once a cell has passed through start, it passes through the remainder of the G1 phase, which is the pre-DNA synthesis phase. The second stage, the S phase, is when DNA synthesis takes place. This is followed by the G2 phase, which is the period between DNA synthesis and mitosis. Mitosis itself occurs at the M phase. Quiescent cells (which include cells in which quiescence has been induced as well as those cells which are naturally quiescent, such as certain fully differentiated cells) are generally regarded as not being in any of these four phases of the cycle; they are usually described as being in a G0 state, so as to indicate that they would not normally progress through the cycle. The nuclei of quiescent G0 cells, like the nuclei of G1 cells, have a diploid DNA content; both of such diploid nuclei can be used in the present invention.

Subject to the above, it is believed that there is no significant limitation on the cells that can be used in nuclear donors: fully or partially differentiated cells or undifferentiated cells can be used as can cells which are cultured in vitro or abstracted ex vivo. The only limitation is that the donor cells have normal DNA content and be karyotypically normal. A preferred source of cells is disclosed in our co-pending PCT patent application No. PCT/GB95/02095, published as WO 96/07732. It is believed that all such normal cells contain all of the genetic information required for the production of an adult animal. The present invention allows this information to be provided to the developing embryo by altering chromatin structure such that the genetic material can re-direct development.

Recipient cells useful in the invention are enucleated oocytes which are arrested in the metaphase of the second meiotic division. In most vertebrates, oocyte maturation proceeds in vivo to this fairly late stage of the egg maturation process and then arrests. At ovulation, the arrested oocyte is released from the ovary (and, if fertilisation occurs, the oocyte is naturally stimulated to complete meiosis). In the practice of the invention, oocytes can be matured either in vitro or in vivo and are collected on appearance of the 1st polar body or as soon as possible after ovulation, respectively.

It is preferred that the recipient be enucleate. While it has been generally assumed that enucleation of recipient oocytes in nuclear transfer procedures is essential, there is no published experimental confirmation of this judgement. The original procedure described for ungulates involved splitting the cell into two halves, one of which was likely to be enucleated (Willadsen *Nature* 320 (6) 63–65 (1986)). This procedure has the disadvantage that the other unknown half will still have the metaphase apparatus and that the reduction in volume of the cytoplasm is believed to accelerate the pattern of differentiation of the new embryo (Eviskov et al., *Development* 109 322–328 (1990)).

More recently, different procedures have been used in attempts to remove the chromosomes with a minimum of cytoplasm. Aspiration of the first polar body and neighbouring cytoplasm was found to remove the metaphase II apparatus in 67% of sheep oocytes (Smith & Wilmut *Biol. Reprod.* 40 1027–1035 (1989)). Only with the use of DNA-specific fluorochrome (Hoechst 33342) was a method provided by which enucleation would be guaranteed with the minimum reduction in cytoplasmic volume (Tsunoda et al., *J. Reprod. Fertil.* 82 173 (1988)). In livestock species, this is probably the method of routine use at present (Prather & First *J. Reprod. Fertil. Suppl.* 41 125 (1990), Westhusin et al., *Biol. Reprod. (Suppl.)* 42 176 (1990)).

There have been very few reports of non-invasive approaches to enucleation in mammals, whereas in amphibians, irradiation with ultraviolet light is used as a routine procedure (Gurdon Q. *J. Microsc. Soc.* 101 299–311 (1960)). There are no detailed reports of the use of this approach in mammals, although during the use of DNA-specific fluorochrome it was noted that exposure of mouse oocytes to ultraviolet light for more than 30 seconds reduced the developmental potential of the cell (Tsunoda et al., *J. Reprod. Fertil.* 82 173 (1988)).

As described above enucleation may be achieved physically, by actual removal of the nucleus, pro-nuclei or metaphase place (depending on the recipient cell), or functionally, such as by the application of ultraviolet radiation or another enucleating influence.

After enucleation, the donor nucleus is introduced either by fusion to donor cells under conditions which do not induce oocyte activation or by injection under non-activating conditions. In order to maintain the correct ploidy of the reconstructed embryo the donor nucleus must be diploid (i.e. in the G0 or G1 phase of the cell cycle) at the time of fusion.

Once suitable donor and recipient cells have been prepared, it is necessary for the nucleus of the former to be transferred to the latter. Most conveniently, nuclear transfer is effected by fusion. Activation should not take place at the time of fusion.

Three established methods which have been used to induce fusion are:

(1) exposure of cells to fusion-promoting chemicals, such as polyethylene glycol;
(2) the use of inactivated virus, such as Sendai virus; and
(3) the use of electrical stimulation.

Exposure of cells to fusion-promoting chemicals such as polyethylene glycol or other glycols is a routine procedure for the fusion of somatic cells, but it has not been widely used with embryos. As polyethylene glycol is toxic it is necessary to expose the cells for a minimum period and the need to be able to remove the chemical quickly may necessitate the removal of the zona pellucida (Kanka et al., *Mol. Reprod. Dev.* 29 110–116 (1991)). In experiments with mouse embryos, inactivated Sendai virus provides an efficient means for the fusion of cells from cleavage-stage embryos (Graham *Wistar Inst. Symp. Monogr.* 9 19 (1969)), with the additional experimental advantage that activation is not induced. In ungulates, fusion is commonly achieved by the same electrical stimulation that is used to induce parthogenetic activation (Willadsen *Nature* 320 (6) 63–65 (1986), Prather et al., *Biol. Reprod.* 37 859–866 (1987)). In these species, Sendai virus induces fusion in a proportion of cases, but is not sufficiently reliable for routine application (Willadsen *Nature* 320 (6) 63–65 (1986)).

While cell-cell fusion is a preferred method of effecting nuclear transfer, it is not the only method that can be used. Other suitable techniques include microinjection (Ritchie and Campbell, *J. Reproduction and Fertility* Abstract Series No. 15, p60).

In a preferred embodiment of the invention, fusion of the oocyte karyoplast couplet is accomplished in the absence of activation by electropulsing in 0.3M mannitol solution or 0.27M sucrose solution; alternatively the nucleus may be introduced by injection in a calcium free medium. The age of the oocytes at the time of fusion/injection and the absence of calcium ions from the fusion/injection medium prevent activation of the recipient oocyte.

In practice, it is best to enucleate and conduct the transfer s soon as possible after the oocyte reaches metaphase II. The time that this will be post onset of maturation (in vitro) or hormone treatment (in vivo) will depend on the species. For cattle or sheep, nuclear transfer should preferably take place within 24 hours; for pigs, within 48 hours; mice, within 12 hours; and rabbits within 20–24 hours. although transfer can take place later, it becomes progressively more difficult to achieve as the oocyte ages. High MPF activity is desirable.

Subsequently, the fused reconstructed embryo, which is generally returned to the maturation medium, is maintained without being activated so that the donor nucleus is exposed to the recipient cytoplasm for a period of time sufficient to allow the reconstructed embryo to become capable, eventually, of giving rise to a live birth (preferably of a fertile offspring).

The optimum period of time before activation varies from species to species and can readily be determined by experimentation. For cattle, a period of from 6 to 20 hours is appropriate. The time period should probably not be less than that which will allow chromosome formation, and it should not be so long either that the couplet activates spontaneously or, in extreme cases that it dies.

When it is time for activation, any conventional or other suitable activation protocol can be used. Recent experiments have shown that the requirements for parthogenetic activation are more complicated than had been imagined. It had been assumed that activation is an all-or-none phenomenon and that the large number of treatments able to induce formation of a pronucleus were all causing "activation". However, exposure of rabbit oocytes to repeated electrical pulses revealed that only selection of an appropriate series or pulses and control of the $Ca^{2+}$ was able to promote development of diploidized oocytes to mid-gestation (Ozil *Development* 109 117–127 (1990)). During fertilization there are repeated, transient increases in intracellular calcium concentration (Cutbertson & Cobbold *Nature* 316 541–542 (1985)) and electrical pulses are believed to cause analogous increases in calcium concentration. There is evidence that the pattern of calcium transients varies with species and it can be anticipated that the optimal pattern of electrical pulses will vary in a similar manner. The interval between pulses in the rabbit is approximately 4 minutes (Ozil *Development* 109 117–127 (1990)), and in the mouse 10 to 20 minutes (Cutbertson & Cobbold *Nature* 316 541–542

(1985)), while there are preliminary observations in the cow that the interval is approximately 20 to 30 minutes (Robl et al., in *Symposium on Cloning Mammals by Nuclear Transplantation* (Seidel ed.), Colorado State University, 24–27 (1992)). In most published experiments activation was induced with a single electrical pulse, but new observations suggest that the proportion or reconstituted embryos that develop is increased by exposure to several pulses (Collas & Robl *Biol. Reprod.* 43 877–884 (1990)). In any individual case, routine adjustments may be made to optimise the number of pulses, the field strength and duration of the pulses and the calcium concentration of the medium.

In the practice of the invention, correct ploidy must be maintained during activation. It is desirable to inhibit or stabilise microtubule polymerisation in order to prevent the production of multiple pronuclei, thereby to maintain correct ploidy. This can be achieved by the application of a microtubule inhibitor such as nocodazole at an effective concentration (such as about 5 µg/ml). Colchecine and colcemid are other microtubule inhibitors. Alternatively, a microtubule stabiliser, such as, for example, taxol could be used.

The molecular component of microtubules (tubulin) is in a state of dynamic equilibrium between the polymerised and non-polymerised states. Microtubule inhibitors such as nocodazole prevent the addition of tubulin molecules to microtubules, thereby disturbing the equilibrium and leading to microtubule depolymerisation and destruction of the spindle. It is preferred to add the microtubule inhibitor a sufficient time before activation to ensure complete, or almost complete, depolymerisation of the microtubules. Twenty to thirty minutes is likely to be sufficient in most cases. A microtubule stabiliser such as taxol prevents the breakdown of the spindle and may also therefore prevent the production of multiple pronuclei. Use of a microtubule stabiliser is preferably under similar conditions to those used for microtubule inhibitors.

The microtubule inhibitor or stabiliser should remain present after activation until pronuclei formation. It should be removed thereafter, and in any event before the first division takes place.

In a preferred embodiment of the invention at 30–42 hours post onset of maturation (bovine and ovine, i.e. 6–18 hours post nuclear transfer) the reconstructed oocytes are placed into medium containing nocodazole (5 µg/ml) and activated using conventional protocols. Incubation in nocodazole may be continued for 4–6 hours following the activation stimulus (dependent upon species and oocyte age).

According to a second aspect of the invention, there is provided a viable reconstituted animal embryo prepared by a method as described previously.

According to a third aspect of the invention, there is provided a method of preparing an animal, the method comprising:

(a) reconstituting an animal embryo as described above; and (b) causing an animal to develop to term from the embryo; and (c) optionally, breeding from the animal so formed.

Step (a) has been described in depth above.

The second step, step (b) in the method of this aspect of the invention is to cause an animal to develop to term from the embryo. This may be done directly or indirectly. In direct development, the reconstituted embryo from step (a) is simply allowed to develop without further intervention beyond any that may be necessary to allow the development to take place. In indirect development, however, the embryo may be further manipulated before full development takes place. For example, the embryo may be split and the cells clonally expanded, for the purpose of improving yield.

Alternatively or additionally, it may be possible for increased yields of viable embryos to be achieved by means of the present invention by clonal expansion of donors and/or if use is made of the process of serial (nuclear) transfer. A limitation in the presently achieved rate of blastocyst formation may be due to the fact that a majority of the embryos do not "reprogram" (although an acceptable number do). If this is the case, then the rate may be enhanced as follows. Each embryo that does develop itself can be used as a nuclear donor at the 32–64 cell stage; alternatively, inner cell mass cells can be used at the blastocyst stage. If these embryos do indeed reflect those which have reprogrammed gene expression and those nuclei are in fact reprogrammed (as seems likely), then each developing embryo may be multiplied in this way by the efficiency of the nuclear transfer process. The degree of enhancement likely to be achieved depends upon the cell type. In sheep, it is readily possible to obtain 55% blastocyst stage embryos by transfer of a single blastomere from a 16 cell embryo to a preactivated "Universal Recipient" oocyte. So it is reasonable to hypothesise that each embryo developed from a single cell could give rise to eight at the 16 cell stage. Although these figures are just a rough guide, it is clear that at later developmental stages the extent of benefit would depend on the efficiency of the process at that stage.

Aside from the issue of yield-improving expediencies, the reconstituted embryo may be cultured, in vivo or in vitro to blastocyst.

Experience suggests that embryos derived by nuclear transfer are different from normal embryos and sometimes benefit from or even require culture conditions in vivo other than those in which embryos are usually cultured (at least in vivo). The reason for this is not known. In routine multiplication of bovine embryos, reconstituted embryos (many of them at once) have been cultured in sheep oviducts for 5 to 6 days (as described by Willadsen, In Mammalian Egg Transfer (Adams, E. E., ed.) 185 CRC Press, Boca Raton, Fla. (1982)). In the practice of the present invention, though, in order to protect the embryo it should preferably be embedded in a protective medium such as agar before transfer and then dissected from the agar after recovery from the temporary recipient. The function of the protective agar or other medium is twofold: first, it acts as a structural aid for the embryo by holding the zona pellucida together; and secondly it acts as barrier to cells of the recipient animal's immune system. Although this approach increases the proportion of embryos that form blastocysts, there is the disadvantage that a number of embryos may be lost.

If in vitro conditions are used, those routinely employed in the art are quite acceptable.

At the blastocyst stage, the embryo may be screened for suitability for development to term. Typically, this will be done where the embryo is transgenic and screening and selection for stable integrants has been carried out. Screening for non-transgenic genetic markers may also be carried out at this stage. However, because the method of the invention allows for screening of donors at an earlier stage, that will generally be preferred.

After screening, if screening has taken place, the blastocyst embryo is allowed to develop to term. This will generally be in vivo. If development up to blastocyst has taken place in vitro, then transfer into the final recipient animal takes place at this stage. If blastocyst development has taken place in vivo, although in principle the blastocyst can be allowed to develop to term in the pre-blastocyst host, in practice the blastocyst will usually be removed from the (temporary) pre-blastocyst recipient and, after dissection from the protective medium, will be transferred to the (permanent) post-blastocyst recipient.

In optional step (c) of this aspect of the invention, animals may be bred from the animal prepared by the preceding steps. In this way, an animal may be used to establish a herd or flock of animals having the desired genetic characteristic(s).

Animals produced by transfer of nuclei from a source of genetically identical cells share the same nucleus, but are not strictly identical as they are derived from different oocytes. The significance of this different origin is not clear, but may affect commercial traits. Recent analyses of the mitochondrial DNA of dairy cattle in the Iowa State University Breeding Herd revealed associated with milk and reproductive performance (Freeman & Beitz, In Symposium on Cloning Mammals by Nuclear Transplantation (Seidel, G. E. Jr., ed.) 17–20, Colorado State University, Colorado (1992)). It remains to be confirmed that similar effects are present throughout the castle population and to consider whether it is possible or necessary in specific situations to consider the selection of oocytes. In the area of cattle breeding the ability to produce large numbers of embryos from donors of high genetic merit may have considerable potential value in disseminating genetic improvement through the national herd. The scale of application will depend upon the cost of each embryo and the proportion of transferred embryos able to develop to term.

By way of illustration and summary, the following scheme sets out a typical process by which transgenic and non-transgenic animals may be prepared. The process can be regarded as involving five steps:

(1) isolation of diploid donor cells;
(2) optionally, transgenesis, for example by transfection with suitable constructs, with or without selectable markers;
  (2a) optionally screen and select for stable integrants—skip for micro-injection;
(3) embryo reconstitution by nuclear transfer;
(4) culture, in vivo or in vitro, to blastocyst;
  (4a) optionally screen and select for stable integrants—omit if done at 2a—or other desired characteristics;
(5) transfer if necessary to final recipient.

This protocol has a number of advantages over previously published methods of nuclear transfer:

1) The chromatin of the donor nucleus can be exposed to the meiotic cytoplasm of the recipient oocyte in the absence of activation for appropriate periods of time. This may increase the "reprogramming" of the donor nucleus by altering the chromatin structure.
2) Correct ploidy of the reconstructed embryo is maintained when G0/G1 nuclei are transferred.
3) Previous studies have shown that activation responsiveness of bovine/opine oocytes increases with age. One problem which has previously been observed is that in unenucleated aged oocytes duplication of the meiotic spindle pole bodies occurs and multipolar spindles are observed. However, we report that in embryos reconstructed and maintained with high MPF levels although nuclear envelope breakdown and chromatin condensation occur no organised spindle is observed. The prematurely condensed chromosomes remain in a tight bunch, therefore we can take advantage of the ageing process and increase the activation response of the reconstructed oocyte without adversely affecting the ploidy of the reconstructed embryo.

According to a fourth aspect of the invention, there is provided an animal prepared as described above.

Preferred features of each aspect of the invention are as for each other aspect, *mutatis mutandis*.

The invention will now be described by reference to the accompanying Examples which are provided for the purposes of illustration and are not to be construed as being limiting on the present invention. In the following description, reference is made to the accompanying drawing, in which:

EXAMPLE 1

"MAGIC" Procedure Using Bovine Oocytes

Figure 1:
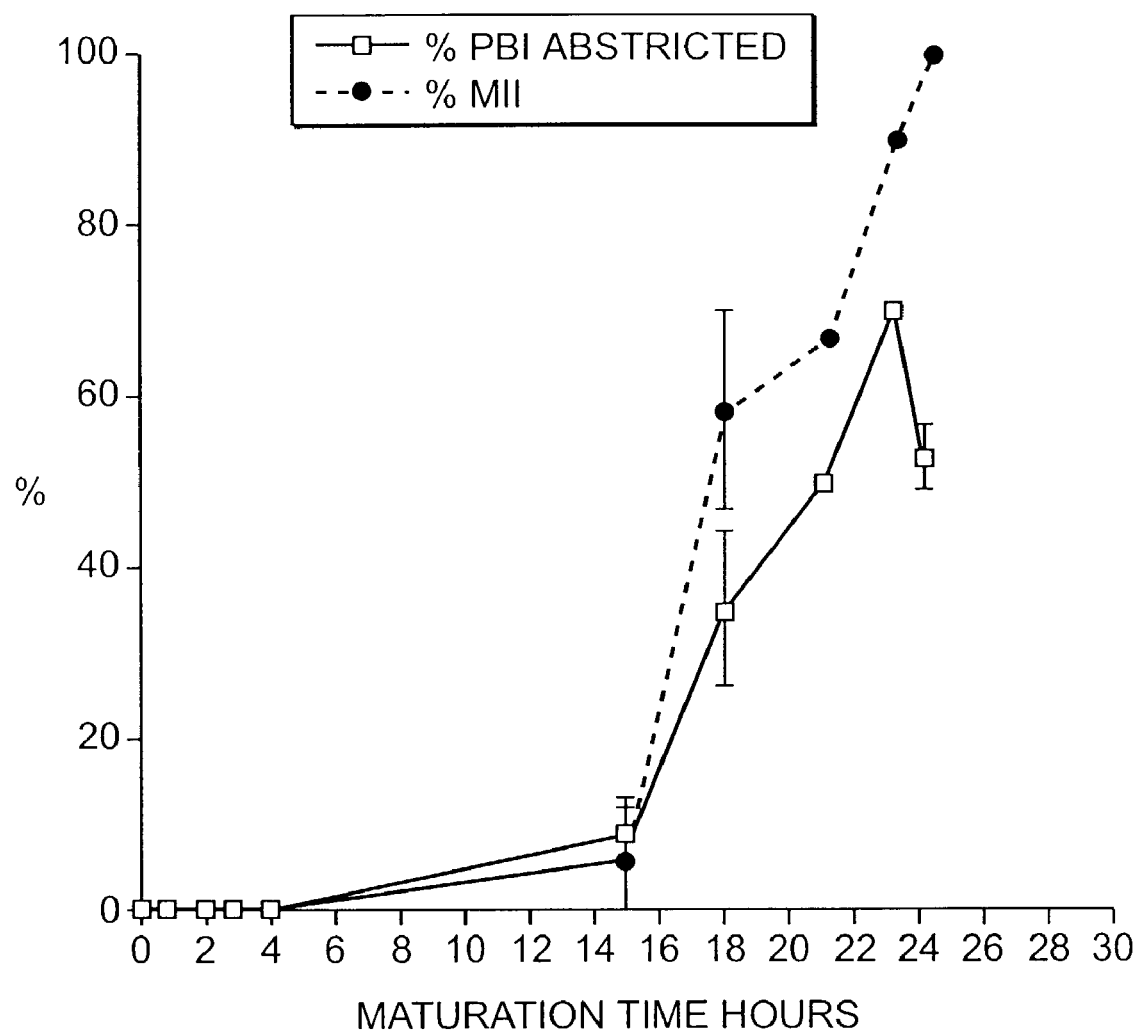
FIG. 1 shows the rate of maturation of bovine oocytes in vitro.

Recipient oocytes the subject of this experimental procedure are designated MAGIC (Metaphase Arrested G1/G0 AcceptIng Cytoplast) Recipients.

The nuclear and cytoplasmic events during in vitro oocyte maturation were studied. In addition the roles of fusion and activation in embryos reconstructed at different ages were also investigated. The studies have shown that oocyte maturation is asynchronous; however, a population of matured oocytes can be morphologically selected at 18 hours (FIG. 1).

Morphological Selection of Oocytes

In FIG. 1 ovaries were obtained from a local abattoir and maintained at 28–32° C. during transport to the laboratory. Cumulus oocyte complexes (COC's) were aspirated from follicles 3–10 mm in diameter using a hypodermic needle (1.2 mm internal diameter) and placed into sterile plastic universal containers. The universal containers were placed into a warmed chamber (35° C.) and the follicular material allowed to settle for 10–15 minutes before pouring off three quarters of the supernatant. The remaining follicular material was diluted with an equal volume of dissection medium (TCM 199 with Earles salts (Gibco), 75.0 mg/l kanamycin, 30.0 mM Hepes, pH 7.4, osmolarity 280 mOsmols/Kg $H_2O$) supplemented with 10% bovine serum, transferred into an 85 mm petri dish and searched for COC's under a dissecting microscope.

Complexes with at least 2–3 compact layers of cumulus cells were selected washed three times in dissection medium and transferred into maturation medium (TC medium 199 with Earles salts (Gibco), 75 mg/l kanamycin, 30.0 mM Hepes, 7.69 mM $NaHCO_3$, pH 7.8, osmolarity 280 mOsmols/Kg $H_2O$) supplemented with 10% bovine serum and $1 \times 10^6$ granulosa cells/ml and cultured on a rocking table at 39° C. in an atmosphere of 5% $CO_2$ in air. Oocytes were removed from the maturation dish and wet mounted on ethanol cleaned glass slides under coverslips which were attached using a mixture of 5% petroleum jelly 95% wax. Mounted embryos were then fixed for 24 hours in freshly prepared methanol:glacial acetic acid (3:1), stained with 45% aceto-orcein (Sigma) and examined by phase contrast and DIC microscopy using a Nikon Microphot-SA, the graph in FIG. 1 shows the percentage of oocytes at MII and those with a visible polar body.

Activation of Bovine Follicular Oocytes

If maturation is then continued until 24 hours these oocytes activate at a very low rate (24%) in mannitol containing calcium (Table 1a). However, removal of calcium and magnesium from the electropulsing medium prevents any activation.

Table 1a shows activation of bovine follicular oocytes matured in vitro for different periods. Oocytes were removed from the maturation medium, washed once in activation medium, placed into the activation chamber and given a single electrical pulse of 1.25 kV/cm for 80 μs.

TABLE 1a

| No. of oocytes (N) | Hours post onset of maturation (hpm) [age (hrs)] | Pronuclear formation (% activation) |
| --- | --- | --- |
| 73 | 24 | 24.6 |
| 99 | 30 | 84.8 |
| 55 | 45 | 92.7* |

*many 2 or more pronuclei

Activation Response of Sham Enucleated Bovine Oocytes

Table 1b shows activation response of in vitro matured bovine oocytes sham enucleated at approximately 22 hours post onset of maturation (hpm). Oocytes were treated exactly as for enucleation, a small volume of cytoplasm was aspirated not containing the metaphase plate. After manipulation the oocytes were given a single DC pulse of 1.25 KV/cm and returned to the maturation medium, at 30 hpm and 42 hpm groups or oocytes were mounted, fixed and stained with aceto-orcein. The results show the number of oocytes at each time point from five individual experiments as the number of cells having pronuclei with respect to the total number of cells.

TABLE 1b

| EXPERIMENT | No. cells having pronuclei/Total no. of cells 30 hpm | No. cells having pronuclei/Total no. of cells 42 hpm |
| --- | --- | --- |
| 1 | 1/8 | — |
| 2 | 0/24 | 0/30 |
| 3 | 0/21 | 0/22 |
| 4 | 0/27 | 0/25 |
| 5 | 0/19 | 0/1 | hpm = hours post onset of maturation

Pronuclear Formation in Enucleated Oocytes

Table 2 shows pronuclear formation in enucleated oocytes fused to primary bovine fibroblasts (24 hpm) and subsequently activated (42 hpm). The results represent five separate experiments. Oocytes were divided into two groups, group A were incubated in nocodazole for 1 hour prior to activation and for 6 hours following activation. Group B were not treated with nocodazole. Activated oocytes were fixed and stained with aceto-orcein 12 hours post activation. The number of pronuclei (PN) in each parthenote was then scored under phase contrast. The results are expressed as the percentage of activated oocytes containing 1 or more pronuclei.

TABLE 2

| | TOTAL | 1 PN | 2 PN | 3 PN | 4 PN | >4 PN |
| --- | --- | --- | --- | --- | --- | --- |
| GROUP A | 52 | 100 | 0 | 0 | 0 | 0 |
| GROUP B | 33 | 45.2 | 25.8 | 16.1 | 3.2 | 9.7 |

The absence of an organised spindle and the absence of a polar body suggests that in order to maintain ploidy in the reconstructed embryo then only a diploid i.e. G0/G1 nucleus should be transferred into this cytoplasmic situation. Incubation of activated oocytes in the presence of the microtubule inhibitor nocodazole for 5 hours, 1 hour prior to and following the activation stimulus prevents the formation of micronuclei (Table 2) and thus when the donor nucleus is in the G0/G1 phase of the cell cycle the correct ploidy of the reconstructed embryo is maintained.

Results

These results show that:

i) these oocytes can be enucleated at 18 hours post onset of maturation (FIG. 1);

ii) enucleated oocytes can be fused to donor blastomeres/cells in either 0.3M mannitol or 0.27M sucrose alternatively the donor the cells or nuclei can be injected in calcium free medium in the absence of any activation response;

iii) reconstructed embryos or enucleated pulsed oocytes can be cultured in maturation medium and do not undergo spontaneous activation;

iv) the transferred nucleus is seen to undergo nuclear envelope breakdown (NEBD) and chromosome condensation. No organised meiotic/mitotic spindle is observed regardless of the cell cycle stage of the transferred nucleus;

v) such manipulated couplets will activate at 30 hours and 42 hours with a frequency equal to unmanipulated control oocytes;

vi) no polar body is observed following subsequent activation, regardless of the cell cycle stage of the transferred nucleus;

viii) upon subsequent activation 1–5 micronuclei are formed per reconstructed zygote (Table 2).

Reconstruction of Bovine Embryos Using "MAGIC" Procedure

In preliminary experiments this technique has been applied to the reconstruction of bovine embryos using primary fibroblasts synchronised in the G0 phase of the cell cycle by serum starvation for five days. The results are summarised in Table 3.

Table 3 shows development of bovine embryos reconstructed by nuclear transfer of serum starved (G0) bovine primary fibroblasts into enucleated unactivated MII oocytes. Embryos were reconstructed at 24 hpm and the fused couplets activated at 42 hpm. Fused couplets were incubated in nocodazole (5 μg/ml) in M2 medium for 1 hour prior to activation and 5 hours post activation. Couplets were activated with a single DC pulse of 1.25 KV/cm for 80 μsec.

TABLE 3

| EXPERIMENT NUMBER | NUMBER OF BLASTOCYSTS/ TOTAL NUMBER OF FUSED COUPLETS | % BLASTOCYSTS |
| --- | --- | --- |
| 1 | 1/30 | 3.3 |
| 2 | 4/31 | 12.9 |

EXAMPLE 2

"MAGIC" Procedure Using Opine Oocytes

Similar observations to those in Example 1 have also been made in opine oocytes which have been matured in vivo. Freshly ovulated oocytes can be retrieved by flushing from the oviducts of superstimulated ewes 24 hours after prostaglandin treatment. The use of calcium magnesium free PBS/1.0% FCS as a flushing medium prevents oocyte activation. Oocytes can be enucleated in calcium free medium and donor cells introduced as above in the absence of activation. No organised spindle is observed, multiple nuclei are formed upon subsequent activation and this may be suppressed by nocodazole treatment.

Results

In preliminary experiments in sheep, a single pregnancy has resulted in the birth of a single live lamb. The results are summarised in Tables 4 and 5.

Table 4 shows development of opine embryos reconstructed by transfer of an embryo derived established cell line to unactivated enucleated in vivo matured opine oocytes. Oocytes were obtained from superstimulated Scottish blackface ewes, the cell line was established from the embryonic disc of a day 9 embryo obtained from a Welsh mountain ewe. Reconstructed embryos were cultured in the ligated oviduct of a temporary recipient ewe for 6 days, recovered and assessed for development.

TABLE 4

| DATE OF NUCLEAR TRANSFER | PASSAGE NUMBER | NUMBER OF MORULA, BLASTOCYSTS/ TOTAL NUMBER |
|---|---|---|
| 17 Jan. 1995 | 6 | 4/28 |
| 19 Jan. 1995 | 7 | 1/10 |
| 31 Jan. 1995 | 13 | 0/2 |
| 02 Feb. 1995 | 13 | 0/14 |
| 07 Feb. 1995 | 11 | 1/9 |
| 09 Feb. 1995 | 11 | 1/2 |
| 14 Feb. 1995 | 12 | |
| 16 Feb. 1995 | 13 | 3/13 |
| TOTAL | | 10/78 (12.8%) |

Table 5 shows induction of pregnancy following transfer of all morula/blastocyst stage reconstructed embryos to the uterine horn of synchronised final recipient blackface ewes. The table shows the total number of embryos from each group transferred the frequency of pregnancy in terms of ewes and embryos, in the majority of cases 2 embryos were transferred to each ewe. A single twin pregnancy was established which resulted in the birth of a single live lamb.

TABLE 5

| PASSAGE NUMBER | "MAGIC" |
|---|---|
| P6 | 4 |
| P7 | 1 |
| P11 | 2 |
| P12 | 0 |
| P13 | 3 |
| TOTAL MOR/BL | 10 |
| TOTAL NUMBER EWES | 6 |
| PREGNANT EWES % | 1 (16.7) |
| FOETUSES/ TOTAL TRANSFERRED (%) | 2/10 (20.0) |

The invention claimed is:

1. A method of serial nuclear transfer comprising:
   (i) providing a transgenic reconstructed ungulate embryo comprising a nucleus from a cultured diploid ungulate differentiated cell, wherein said embryo is capable of cell division;
   (ii) culturing said embryo;
   (iii) splitting said embryo into cells; and
   (iv) inserting the nuclei of said cells into enucleated oocytes of the same species to reconstruct viable embryos.

2. The method of claim 1, wherein said reconstructed embryo comprising a nucleus from a cultured diploid ungulate differentiated cell is cultured to the 32–64 cell stage.

3. The method of claim 1, wherein said reconstructed embryo comprising a nucleus from a cultured diploid ungulate differentiated cell is cultured to the blastocyst stage.

4. The method of claim 1, further comprising clonally expanding said cells.

5. The method of claim 1, wherein the ungulate is a cattle.

6. The method of claim 1, wherein the ungulate is a sheep.

7. The method of claim 1, wherein the ungulate is a pig.

8. The method of claim 1, wherein the ungulate is a goat.

* * * * *